United States Patent [19]
Rao

[11] Patent Number: 5,924,984
[45] Date of Patent: Jul. 20, 1999

[54] ANORECTAL PROBE APPARATUS HAVING AT LEAST ONE MUSCULAR ACTIVITY SENSOR

[75] Inventor: Satish Rao, Iowa City, Iowa

[73] Assignee: University of Iowa Research Foundation, Iowa City, Iowa

[21] Appl. No.: 08/791,313

[22] Filed: Jan. 30, 1997

[51] Int. Cl.⁶ ...................................................... A61B 5/00
[52] U.S. Cl. ........................ 600/373; 600/593; 600/546; 600/587
[58] Field of Search ................................ 600/546, 373, 600/587, 593, 560, 561, 372

[56] References Cited

U.S. PATENT DOCUMENTS

| | | |
|---|---|---|
| 3,599,628 | 8/1971 | Abbenante et al. . |
| 4,396,019 | 8/1983 | Perry, Jr. . |
| 4,809,710 | 3/1989 | Williamson . |
| 4,887,610 | 12/1989 | Mittal . |
| 4,909,263 | 3/1990 | Norris . |
| 5,109,870 | 5/1992 | Silny et al. ............................. 128/780 |
| 5,154,177 | 10/1992 | Eisman et al. . |
| 5,297,437 | 3/1994 | Schneider . |
| 5,411,548 | 5/1995 | Carman . |
| 5,423,329 | 6/1995 | Ergas . |
| 5,433,216 | 7/1995 | Sugure et al. . |
| 5,452,719 | 9/1995 | Eisman et al. .......................... 128/640 |
| 5,533,515 | 7/1996 | Coller et al. . |
| 5,617,876 | 4/1997 | Van Duyl ................................ 128/774 |

OTHER PUBLICATIONS

Brochure from Medical Measurements Incorporated, Copyright 1987.
*A New Technique for Continuous Sphincter Pressure Measurement*, J. Dent, M.A., M.B., B. Chir., F.R.A.C.P., M.R.C.P.; Gastroenterology, vol. 71, No. 2, pp. 263–267.

*Primary Examiner*—William E. Kamm
*Assistant Examiner*—Eleni Mantis Mercader
*Attorney, Agent, or Firm*—Woodard, Emhardt, Naughton, Moriarty &McNett

[57] ABSTRACT

An apparatus for sensing muscular activity of the rectosigmoid region, rectum, and the anorectal canal of a subject is disclosed. This apparatus includes an elongate probe having a distal end opposing a proximal end which is configured for insertion into the patient's anorectal canal and includes a pressure sensor, an electromyography sensor, and a stimulus balloon. Multiple pressure sensors may be included to evaluate muscular activity in the anorectal canal. In addition, pressure sensors may be distributed along the length of the probe to simultaneously measure the response of other portions of the anorectal canal besides the anal sphincter muscle. A pressure sensor is also located inside the stimulus balloon for monitoring intraballoon pressure.

24 Claims, 2 Drawing Sheets

ANORECTAL PROBE APPARATUS HAVING AT LEAST ONE MUSCULAR ACTIVITY SENSOR

BACKGROUND OF THE INVENTION

The present invention relates to probes for assessing and treating medical conditions, and more particularly, but not exclusively, relates to multi-sensor probes for defecation disorders.

Defecation disorders, such as constipation and fecal incontinence, affect as many as 20% of the population. Evaluating muscle activity of the defecation unit, including those of the anus, rectum, and rectosigmoid regions, is generally an effective way to diagnose these disorders and plan appropriate treatment. Various treatments, such as biofeedback therapy, also utilize an anorectal probe or catheter having these capabilities.

U.S. Pat. Nos. 5,533,515 to Coller et al, and 4,887,610 to Mittal provide background information concerning devices to monitor selected aspects of sphincter muscle activity. However, there remains a need for a comprehensive probe to simultaneously monitor pressure and electrical activity of anorectal muscles at different locations in order to fully assess and treat various defecation disorders. Furthermore, a way to controllably stimulate appropriate anorectal muscles relative to the desired monitoring locations is needed.

SUMMARY OF THE INVENTION

The present invention relates to a probe apparatus configured for insertion in a body lumen to assess and treat medical conditions. Various aspects of the invention are novel, non-obvious, and provide distinct advantages. Although the actual nature of the invention covered herein can only be determined with reference to the claims appended hereto, certain features which are characteristic of the preferred embodiment disclosed herein can be described briefly as follows.

One feature of the present invention is an anorectal monitoring apparatus having an elongate probe which is configured for insertion in a patient's anorectal canal. The probe has multiple sensors to detect pressure and electrical activity of the muscles of the anorectal canal. A stimulus balloon may be affixed to the probe which may be distended by a pressurized fluid, such as pressurized air, to stimulate muscle activity in the anorectal canal. As used herein, a "fluid" may be a liquid or a gas. Thus, this single probe apparatus facilitates assessments of anorectal sensation and simultaneous recording of pressure and electrical activity without resorting to multiple probes or catheters.

In another feature of the present invention, an anorectal monitoring apparatus includes an elongate probe which has a pressure sensor to monitor muscular activity in the anorectal canal at a corresponding location. A stimulus balloon is carried on the probe and proximally spaced apart from this location. The balloon is configured to provide selective stimulation of the rectum when inflated. This arrangement facilitates monitoring anal sphincter muscle activity at a location distal to the stimulus.

In still another feature of the present invention an apparatus senses muscular activity in an anorectal canal of a patient and includes an elongate probe with at least three pressure sensors coupled thereto. These sensors are configured to simultaneously monitor anal sphincter activity of the patient at each of a number of corresponding positions on the probe. These positions are each within about a three centimeter length along the probe and are circumferentially and longitudinally spaced apart from each other. An electromyography sensor is also coupled to the probe. The electromyography sensor simultaneously monitors anal sphincter activity within about one centimeter of at least one of the positions corresponding to the pressure sensors. This arrangement has been found to be particularly advantageous for monitoring both the pressure and the electrical activity of the anal sphincter.

Accordingly, it is one object of the present invention to provide an apparatus with a multi-sensor probe for evaluating the performance of a patient's anorectal canal.

It is another object of the present invention to provide a probe which includes a sensing location distal to a stimulus device.

It is still another object of the present invention to provide an electromyography sensor and multiple pressure sensors in an arrangement particularly suited for monitoring a patient's internal and external anal sphincter activity simultaneously.

Further objects, features, advantages, and aspects of the present invention will become apparent from the detailed descriptions and drawings contained herein.

DETAILED DESCRIPTION OF THE PREFERRED EMBODIMENT

Figure 1:
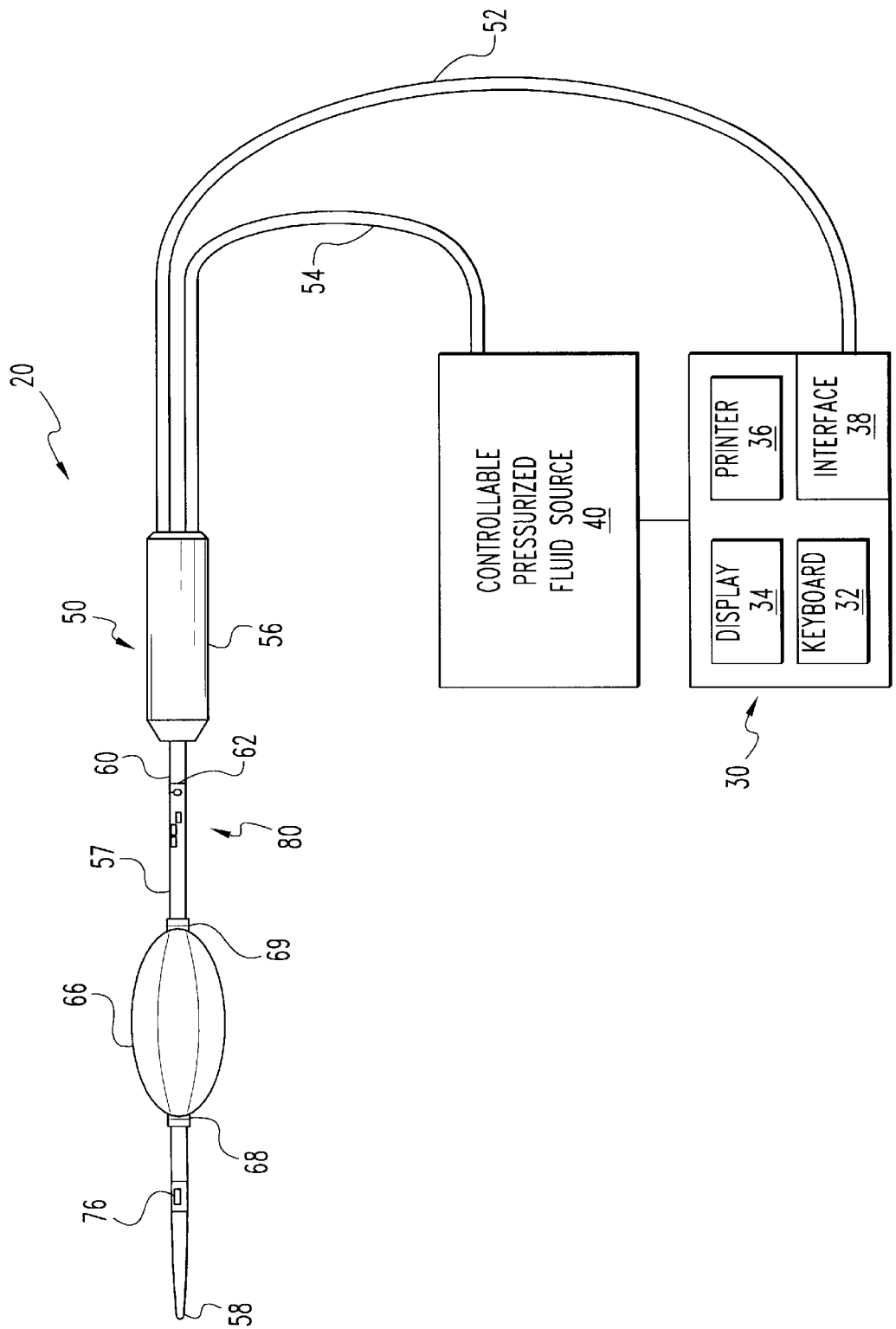
FIG. 1 is a partial schematic view of one embodiment of an anorectal monitoring system of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and further modifications in the described device, and any further applications of the principles of the invention as described herein are contemplated as would normally occur to one skilled in the art to which the invention relates.

FIG. 1 illustrates an anorectal monitoring system 20 of one embodiment of the present invention. System 20 includes monitor/controller 30 and controllable pressurized fluid source 40 operatively coupled to probe 50.

Monitor/controller 30 is preferably a digital processor configured to execute various software instructions loaded therein. Monitor/controller 30 includes input keyboard 32 and video display 34. Also, monitor/controller 30 has printer 36 coupled thereto. Interface 38 of monitor/controller 30 is operatively coupled to probe 50 by cable 52.

Monitor/controller 30 is also operatively coupled to controllable pressurized fluid source 40. Controllable pressurized fluid source 40 is connected to probe 50 by conduit 52. Probe 50 includes elongate body 57 with distal end portion 58 opposing proximal end portion 60. Proximal end portion 60 has anal margin mark 62 used to determine position of probe 50 relative to a patient's anorectal canal. Probe 50 also includes stimulus balloon 66 coupled between distal end portion 58 and proximal end portion 60. Balloon 66 is held in place by tie rings 68 and 69.

Figure 2:
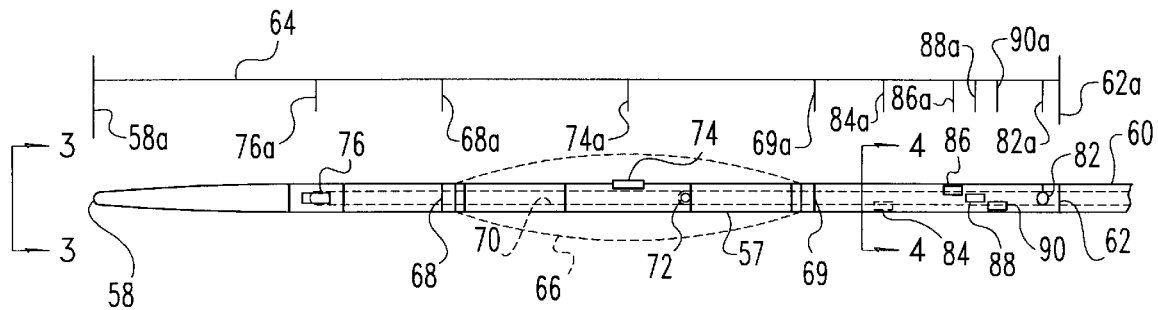
FIG. 2 is a partial side view showing various aspects of the probe of the embodiment of FIG. 1 in greater detail.

Referring additionally to FIG. 2, a portion of probe 50 is shown in greater detail. Probe 50 defines lumen 70 along its length which is in fluid communication with balloon 66 via opening 72 to provide for the delivery of pressurized air or another fluid to balloon 66 (balloon 66 is shown in phantom in FIG. 2). Besides opening 72, pressure sensor 74 is also located within balloon 66. Sensor 74 is used to monitor pressure within balloon 66 (intraballoon pressure). Distal to balloon 66 and sensor 74 is pressure sensor 76.

Referring to longitudinal reference segment 64, preferably the length of probe 50 from anal margin mark 62 to the distal end is about 16 centimeters. This length corresponds to the distance between tick marks 58a and 62a. Tick mark 76a corresponds generally to the center of sensor 76 and preferably represents a distance from tick mark 62a of about 14 centimeters. Also, the distance from mark 62 to the center of sensor 74 is preferably about 9 centimeters, as indicated by the distance between tick marks 62a and 74a. Tie rings 68, 69 correspond to tick marks 68a, 69a which are preferably 11 and 7 centimeters from tick mark 62a, respectively.

Figure 3:
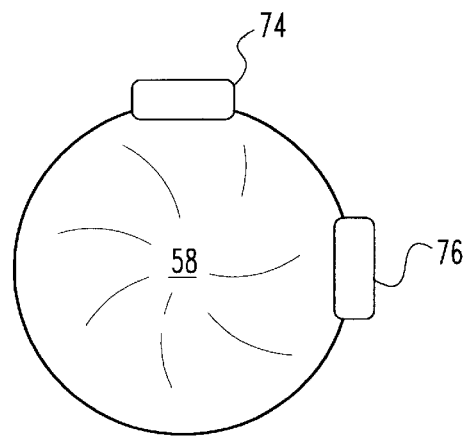
FIG. 3 is an end elevational view of the probe shown in FIG. 2.

Referring additionally to FIG. 3, the circumferential spacing of sensors 74 and 76 is indicated. Preferably, about 25% of the distance along the circumference of probe 50 separates sensors 74 and 76. For the generally circular circumference of distal end portion 58 illustrated in FIG. 3, the spacing between 74 and 76 corresponds to an angular separation of about 90 degrees.

Region 80 refers to a part of proximal end portion 60 of probe 50 which is distal to anal margin mark 62. Preferably, region 80 is encompassed by a length along segment 64 of no more than 4 centimeters. More preferably, region 80 corresponds to a length of no more than 3 centimeters. Generally, region 80 corresponds to the length required to monitor the anal sphincter muscle for most patients.

Figure 4:
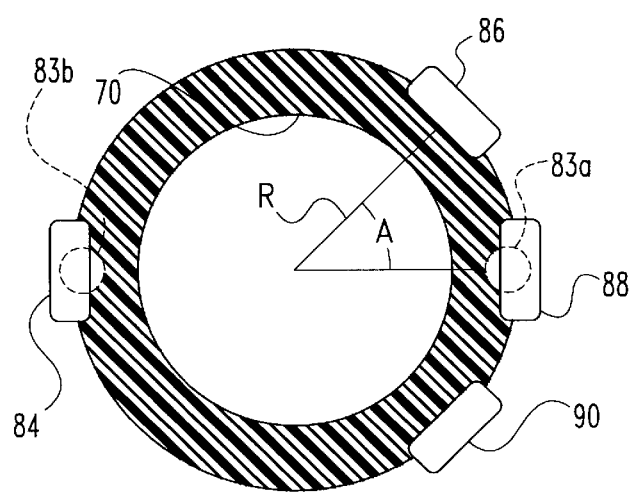
FIG. 4 is a cross-sectional view of the probe of FIG. 2.

Referring to FIGS. 2 and 4, region 80 includes electromyography (EMG) sensor 82 comprising electrodes 83a and 83b. Preferably, electrodes 83a, 83b are of a platinum, silver, or silver chloride variety. EMG sensor 82 is preferably centered no more than one centimeter from anal margin mark 62 as indicated by the distance between tick marks 62a and 82a along segment 64. More preferably, the distance between tick marks 62a and 82a is about 0.5 centimeters. Besides EMG sensor 82, region 80 also includes a number of proximal pressure sensors 84, 86, 88, 90 with corresponding central tick marks 84a, 86a, 88a, 90a along segment 64 (sensor 84 is shown in phantom in FIG. 2). Preferably, the center-to-center spacing of these sensors from one to the next along segment 64 is no more than about 1 centimeter. More preferably, tick mark 90a is about 0.5 centimeter from tick mark 82a and about 1 centimeter from tick mark 62a. Similarly, tick mark 88a is more preferably spaced apart from tick mark 62a by about 1.5 centimeters along segment 64. Also, tick mark 86a corresponding to pressure signal 86 is more preferably spaced apart from tick mark 62a by about 2 centimeters along segment 64. In addition, it is more preferred that tick mark 84a be spaced apart from tick mark 62a by no more than about 3 centimeters along segment 64.

FIG. 2 generally illustrates the longitudinal spacing of the region 80 sensors along probe 50 relative to segment 64. FIG. 4 generally shows the circumferential spacing of the region 80 sensors. Referring to FIG. 4, electrodes 83a and 83b are preferably on opposite sides of probe 50 (shown in phantom in FIG. 4). This spacing generally corresponds to a 180 degree separation. Similarly, pressure sensor 84 is opposed to pressure sensor 88 which corresponds to an approximate 180 degree separation. For the generally circular cross-section of region 80 shown in FIG. 4, radius R is shown and the resulting angular separation between sensors 86 and 88 is illustrated as angle A. Preferably, angle A is less than 90 degrees. More preferably, angle A is about 60 degrees. Similarly, it is more preferred that about 60 degrees separate sensors 88 and 90. It should be understood that sensors 84, 86, 88, 90 preferably follow a generally helical path about probe 50. It has been found that this arrangement of sensors provides an ideal way to characterize the function of anal sphincter muscles for most patients.

Preferably, elongate body 57 of probe 50 is manufactured from an organic polymeric resin of the thermoplastic or thermoset type. Furthermore, it is preferred that balloon 66 be made of a resilient material of natural or synthetic origin. Tie rings 68 and 69 are preferably formed from a metal which is X-ray opaque, but alternatively may be made from another material which would occur to one skilled in the art. Pressure sensors 74, 76, 84, 86, 88, and 90 are preferably of a pressure transducer variety commonly used for monitoring muscular activity. It is preferred that electrodes 83a, 83b be made from a platinum, silver, or silver chloride material which is affixed to elongate probe body 57. In other embodiments of probe 50, it is envisioned that different arrangements and spacing of the sensors, and alternative materials may be used to construct probe 50 as would occur to one skilled in the art.

Referring generally to FIGS. 1–4, operation of system 20 is next discussed. The patient is prepared by evacuating the bowel using conventional procedures. System 20 is operated by activating monitor/controller 30 and inserting elongate body 57 of probe 50 into the anorectal canal through the patient's anus. Insertion is continued with distal end portion 58 advancing through the anorectal canal until the anal margin of the patient aligns with anal margin mark 62. In this position, pressure sensor 76 is configured to monitor activity of the anorectal canal distal to the anal sphincter and sensors of region 80 are aligned in a desired relationship to simultaneously provide signals corresponding to electrical and mechanical muscle activity of the anus. Signals from sensors 74, 76, 82, 84, 86, 88, and 90 are provided by a coupling through lumen 70 (not shown) which continues from probe 50 through cable 52 to monitor/controller 30. These signals may be in an analog format, digital format, or a hybrid combination of both in accordance with the type of sensor providing the signal. Interface 38 is configured to receive and record these signals, providing amplification and other conditioning as required. Preferably, the signals are stored as data in monitor/controller 30, and monitor/controller 30 executes software to process this data and thereby provide a visual display of graphical information corresponding to anorectal muscular activity of the patient. This display may include graphical results provided by execution of vectorgraphy software known to those skilled in the art. Visual output may also be supplied by printing a hardcopy with printer 36.

Control over the execution of software and other functions may be provided via keyboard 32 of monitor/controller 30. To stimulate muscular activity within the patient, it is preferred that balloon 66 be inflated. To control inflation of balloon 66, preferably monitor/controller 30 sends a signal to controllable pressurized fluid source 40 to output pressurized fluid, preferably air, through conduit 54 which is in fluid communication with lumen 70. The pressurized fluid passes through lumen 70 and opening 72 to enter balloon 66 and thereby inflate it. Besides air, a liquid or other gaseous composition may serve as the pressurized fluid.

The muscular response of the patient to the inflation of balloon 66 is then measured with the sensors of probe 50 and corresponding results are evaluated with monitor/controller 30. By coupling monitor/controller 30 to source 40, the timing relationships between stimulus and patient muscular response may be accurately measured and graphically displayed.

System 20 provides a unique way to simultaneously evaluate muscular activity distal to the stimulus device as well as proximal to the stimulating device. Moreover, system 20 provides mechanical pressure response of the anal sphincter muscle at a number of different positions corresponding to different longitudinal and circumferential sites along body 57. Concurrently, electrical activity of the anal sphincter muscle may be measured with electromyography sensor 82. This unique integrated approach to measurement of muscular activity in the anorectal canal provides a multi-variable evaluation not possible with existing devices.

All publications, patents, and patent applications cited in this specification are herein incorporated by reference as if each individual publication, patent, or patent application were specifically and individually indicated to be incorporated by reference and set forth in its entirety herein.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus configured for sensing muscular activity in an anorectal canal of a patient, comprising: an elongate probe having a distal end opposing a proximal end, said probe being configured for insertion into the patient's anorectal canal, said probe defining a lumen configured for passage of pressurized fluid therethrough, said probe including:

(a) a first pressure sensor configured to provide a pressure signal representative of muscular activity in the anorectal canal;
    (b) an electromyography sensor configured to provide an electromyography signal representative of muscular activity in the anorectal canal;
    (c) a stimulus balloon carried on said probe, said balloon being in fluid communication with said lumen, said balloon being configured to stimulate muscle activity in the anorectal canal when inflated with pressurized fluid delivered through said lumen; and
    wherein said first pressure sensor is positioned on said probe between said distal end and said balloon.

2. The apparatus of claim 1, wherein said electromyography sensor is provided by a pair of opposing electrodes positioned proximal to said balloon.

3. The apparatus of claim 1, further comprising a second pressure sensor positioned along said probe between said balloon and said proximal end.

4. The apparatus of claim 1, wherein said probe is generally cylindrical and further comprising a plurality of second pressure sensors, said second pressure sensors being arranged along a helical path on said probe proximal to said balloon.

5. The apparatus of claim 1, further comprising a plurality of second pressure sensors of at least three in number, said second pressure sensors are spaced apart from one another along a longitudinal portion of said probe, said portion having a length of no more than about two centimeters.

6. The apparatus of claim 1, further comprising a monitoring device responsive to said pressure signal and said electromyography signal to provide a visual output representative of muscular activity in the anorectal canal.

7. The apparatus of claim 1, further comprising a controllable pressurized fluid source in fluid communication with said lumen of said probe to selectively inflate said balloon.

8. An apparatus configured for sensing muscular activity in an anorectal canal of a patient, comprising: an elongate probe having a distal end portion and a proximal end portion, said probe being configured for insertion into the anorectal canal, said probe defining a lumen configured for passage of pressurized fluid therethrough, said probe including:

(a) a first pressure sensor configured to provide a first pressure signal corresponding to muscular activity in the anorectal canal at a first site; and
    (b) a stimulus balloon carried on said probe and proximally spaced apart from said first site, said balloon being in fluid communication with said lumen and being configured to stimulate muscle activity in the anorectal canal when inflated with pressurized fluid delivered through said lumen.

9. The apparatus of claim 8, further comprising a controllable pressurized fluid source in fluid communication with said lumen of said probe to selectively inflate said balloon.

10. The apparatus of claim 8, further comprising a monitoring device responsive to said first signal to provide a visual output representative of muscular activity in the anorectal canal.

11. The apparatus of claim 8, further comprising a second pressure sensor configured to provide a second pressure signal corresponding to muscle activity at a second site, said second site being proximal to said balloon.

12. The apparatus of claim 8, further comprising a pair of electrodes located proximal to said balloon to monitor muscle activity in the anorectal canal.

13. An apparatus configured for sensing muscular activity in an anorectal canal of a patient, comprising:

(a) an elongate probe having a longitudinal axis with a distal end and a proximal end oppositely disposed therealong, said probe being configured for insertion into the patient's anorectal canal;
    (b) at least three proximal pressure sensors each coupled to said probe, said proximal pressure sensors being configured to simultaneously monitor anal sphincter activity of the patient at each of a corresponding number of different positions, said positions each being within about a three centimeter length along said longitudinal axis and being circumferentially and longitudinally spaced apart from each other; and
    (c) an electromyography sensor coupled to said probe, said electromyography sensor being configured to monitor anal sphincter activity simultaneously with said proximal pressure sensors at a site on said probe located within about one centimeter of at least one of said positions.

14. The apparatus of claim 13, wherein said probe includes a lumen and further comprising:

a stimulus balloon carried on said probe between said distal end and said proximal end, said balloon being in fluid communication with said lumen; and
    a controllable pressurized fluid source in fluid communication with said lumen of said probe to selectively inflate said balloon to stimulate anal sphincter activity.

15. The apparatus of claim 13, further comprising a first distal pressure sensor coupled to said probe, said first distal pressure sensor being configured to measure muscle activity in the anorectal canal at a first location on said probe distally displaced along said longitudinal axis from said positions by at least about nine centimeters.

16. The apparatus of claim 15, further comprising:

a second distal pressure sensor coupled to said probe, said second distal pressure sensor being configured to measure muscle activity in the anorectal canal at a second location on said probe between said first distal pressure sensor and said proximal pressure sensors; and a stimulus balloon carried on said probe between said first distal pressure sensor and said proximal pressure sensors.

17. The apparatus of claim 13, wherein:

said proximal pressure sensors and said corresponding positions number at least four;

said corresponding positions include a first one centered about 0.5 centimeter distal to said site, a second one centered about 1.0 centimeter distal to said site, a third one centered about 1.5 centimeters distal to said site, and a fourth one centered about 2.5 centimeters distal to said site.

18. The apparatus of claim 17, wherein said probe includes an anal margin mark located about 0.5 centimeter proximal to said site, said positions are generally located along a helical path about said probe; and further comprising:

a first distal pressure sensor coupled to said probe, said first distal pressure sensor being configured to measure muscle activity in the anorectal canal at a first location centered about 9 centimeters from said mark;

a second distal pressure sensor coupled to said probe, said second distal pressure sensor being configured to measure muscle activity in the anorectal canal at a second location centered about 14 centimeters from said mark; and a stimulus balloon carried on said probe between said second distal pressure sensor and said proximal pressure sensors.

19. An apparatus configured for sensing muscular activity in an anorectal canal of a patient, comprising: an elongate probe having a distal end opposing a proximal end, said probe being configured for insertion into the patient's anorectal canal, said probe defining a lumen configured for passage of pressurized fluid therethrough, said probe including:

(a) a stimulus balloon carried on said probe to stimulate muscle activity in the anorectal canal when inflated with pressurized fluid delivered through said lumen;

(b) a first sensor positioned along said probe distal to said balloon to provide a first signal representative of muscular activity in the anorectal canal;

(c) a second sensor positioned along said probe proximal to said balloon to provide a second signal representative of muscular activity in the anorectal canal; and (d) a monitoring device responsive to said first and second signals to provide an output simultaneously representing muscular activity of the anorectal canal at a distal site and a proximal site relative to a location stimulated by said balloon to facilitate diagnosis of defecation disorders.

20. The apparatus of claim 19, wherein said first sensor is a pressure sensor.

21. The apparatus of claim 19, wherein said second sensor is an electromyography sensor including a pair of opposing electrodes.

22. The apparatus of claim 19, further comprising at least three pressure sensors coupled to said probe, said pressure sensors being positioned proximal to said stimulus balloon along said probe.

23. The apparatus of claim 22, wherein said pressure sensors are generally arranged along a helical path about said probe.

24. The apparatus of claim 22, wherein said probe includes an anal margin mark located proximal to said stimulus balloon.

* * * * *